United States Patent
Behera et al.

(10) Patent No.: US 8,712,935 B2
(45) Date of Patent: Apr. 29, 2014

(54) EVOLUTIONARY CLUSTERING ALGORITHM

(75) Inventors: Narayan Behera, Bangalore (IN); Shruti Sinha, Patna (IN); Rakesh Gupta, Vijaipur (IN); Ann Geoncy, Dar Es Salaam (IN); Nevenka Dimitrova, Pelham Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 233 days.

(21) Appl. No.: 13/143,420

(22) PCT Filed: Dec. 23, 2009

(86) PCT No.: PCT/IB2009/055929
§ 371 (c)(1),
(2), (4) Date: Sep. 29, 2011

(87) PCT Pub. No.: WO2010/079402
PCT Pub. Date: Jul. 15, 2010

(65) Prior Publication Data
US 2012/0016826 A1    Jan. 19, 2012

(30) Foreign Application Priority Data
Jan. 6, 2009    (EP) .................................... 09150089

(51) Int. Cl.
*G06N 5/00*    (2006.01)
(52) U.S. Cl.
USPC ............................................. 706/13; 706/45
(58) Field of Classification Search
USPC ..................................................... 706/13, 45
See application file for complete search history.

(56) References Cited

PUBLICATIONS

Fiori, Extraction of biological knowledge by means of data mining techniques, Doctoral Thesis, Politecnico Di Torino, 2010, pp. 1-157.*
P.C. H. Ma et al, "An Evolutionary Clustering Algorithm for Gene Expression Microarray Data Analysis" IEEE Transactions on Computation, vol. 10, No. 3, Jun. 2006, pp. 296-314.
Han-Saem Park et al., "Evolutionary Fuzzy Clustering Algorithm With Knowledge-Based Evaluation and Applications for Gene Expression Profiling" Journal of Computational and Theoretical Nanoscience, vol. 2, No. 4, 2005, pp. 1-10.
Au et al., "Attribute Clustering for Grouping, Selection, and Classification of Gene Expression Data", IEEE/ACM Transactions on Computational Biology and Bioinformatics, vol. 2, No. 2, Apr.-Jun. 2005, pp. 83-101.
By Liu et al., "A Global Optimal Algorithm for Class-Dependent Discretization of Continuous Data", Nov. 19, 2003, pp. 1-25.
Tsutsumi et al., Global Gene Expression Analysis of Gastric Cancer by Oligonucleotide Microarrays. Cancer Research; Jan. 1, 2002 1; 62(1)233-40, pp. 1-12.

(Continued)

*Primary Examiner* — Wilbert L Starks (57) ABSTRACT

The invention relates to selecting a set of candidate genes from a pool of genes. The method comprising receiving a set of gene data; arranging the set of gene data into a set of clusters with similar profiles by use of a clustering algorithm; and inputting the set of clusters into a genetic algorithm to select a set of candidate genes from the set of clusters. The method thus relates to hybrid between selection by clustering computation and selection by evolutionary computation. This hybrid is also referred to as an evolutionary clustering algorithm (ECA).

20 Claims, 3 Drawing Sheets

(56) References Cited

PUBLICATIONS

Alon et al., Broad Patterns of Gene Expression Revealed by Clustering Analysis of Tumor and Normal Colon Tissues Probed by Oligonucleotide Arrays. Proc. Nat'l Academy of Sciences of the United States of America. vol. 96, Jun. 1999, 96(12), pp. 6745-6750.

MacDonald et al., Expression Profiling of Medulloblastoma: PDGFRA and the RAS/MAPK Pathway as Therapeutic Targets for Metastatic Desease. Nat Genet;(2): 2001, pp. 143-152.

Komatsu, Takayuki "On the Characteristics of Amount of Information in Binary Exponential Family", The Institute of Electronics, Information and Communication Engineers, vol. J83-A, No. 5, May 2000.

Odawara, Masaru et al "Feature Selection based on Genetic Algorithm with Mutual Information Filtering", The Institute of Electronics, Information and Communication Engineers and Systems Society, Aug. 2008.

* cited by examiner

EVOLUTIONARY CLUSTERING ALGORITHM

FIELD OF THE INVENTION

The invention relates to selecting a set of candidate genes from a pool of genes, and in particular to selection of candidate genes by use of clustering and evolutionary computing.

BACKGROUND OF THE INVENTION

Clustering and gene selection from microarray gene expressions data have gained tremendous importance since they help in identifying the genes that play pivotal roles in specified biological conditions that lead to diseased states.

In a microarray sampling, RNA samples are hybridized to known cDNAs/oligo probes on the arrays. Normally either spotted microarrays or oligonucleotide microarrays are used, and the user can chose the probes to be spotted according to the specific experimental needs. In oligonucleotide microarrays, short DNA oligonucleotides that match parts of sequence of known mRNA are spotted onto the array. They give estimation of absolute values of gene expression.

Clustering algorithms operating on microarray gene expression data can help in identifying co-regulated and co-expressed genes under certain specified conditions. Thereby help in identifying genes that can classify test samples into diseased and normal classes. Many clustering algorithms have been developed, including the K-means algorithm, the self-organizing map (SOM) algorithm, hierarchical cluster algorithms, bi-cluster algorithms, etc. Clustering algorithms use the differences of the gene expression values to cluster the genes. The difference is expressed in the terms of a distance measure, and conventionally Eucledian distance and Pearson's correlation coefficient is used to calculate similarity between two genes. However, these types of distance measures have some limitations relating to similarities in profile shape, sensitivity to outliers, moreover the number of clusters has to be specified initially.

At least some of these limitations are met by the method called Attribute Clustering Algorithm (ACA) as published by Au et al. in *IEEE/ACM Transactions on Computational Biology and Bioinformatics* 2(2), p. 83-101 (2005). The ACA essentially used the K-means algorithm concept. However, the distance measure employed is an information theoretic measure, as so-called interdependence redundancy measure, that takes into account interdependence between genes.

Another type of algorithm used in bioinformatics, is the Genetic Algorithm (GA), which is a search technique used to find true or approximate solutions to optimization problems. The genetic algorithm starts from a population of randomly generated individuals, i.e. possible solutions, and proceeds in successive generations in finding better solutions. In each generation, every individual in the population is modified to form a new individual. The algorithm is an iterative algorithm, that terminates after a maximum number of generations or when a generation fulfils a given fitness criteria.

While a number of methods have been found to help in identifying candidate genes that can be used as classifiers for given biological conditions, there is still a need in the art to find alternative solutions to further gain insight into the complexity of understanding biological conditions based on gene data.

SUMMARY OF THE INVENTION

The present invention relates to methods and systems for identifying candidate genes from a pool of genes for classification of subjects based on gene data. In particular it is an object of the present invention to provide an alternative or an improved solution with respect to known solutions. To this end, it may be seen as an object of the present invention to provide a solution which is superior over known solution for identification of candidate genes to correctly classify gene data into diseased and normal classes.

According to a first aspect of the present invention there is provided, a method for selecting a set of candidate genes from a pool of genes, the method comprising:
 receiving a set of gene data;
 arranging the set of gene data into a set of clusters with similar profiles by use of a clustering algorithm; and
 inputting the set of clusters into a genetic algorithm to select a set of candidate genes from the set of clusters.

The method relates to hybrid between selection by clustering computation and selection by evolutionary computation. This hybrid is also referred to as an evolutionary clustering algorithm (ECA). An effective method is thereby provided which combines the strengths of clustering methods and evolutionary methods to facilitate the search of candidate genes that qualify to contain the most information for medical diagnostics, and thereby improve the search of finding co-regulated and co-expressed genes under certain conditions. An alternative and improved algorithm is thereby provided which can be used to classify test samples into diseased and normal classes.

In embodiments, the clustering algorithm employs an interdependence redundancy measure as distance measure. It has been found that this distance measure meets some of the limitations and problems of the traditionally distance measures, e.g. the Eucledian/Pearsons's-based distance measures, such as problems relating to limitations arising out of biased initial distribution of genes in the clusters.

In embodiments, a set of individuals are inputted into the genetic algorithm, wherein each individual comprises a set of individual genes, the set of individual genes being generated by assigning to the corresponding gene from the gene data to the indices and the value at each index to the cluster to which the gene is assigned. The individual genes are thus an extension of the traditional genes of a genetic algorithms, since the layer of the clusters has been added to the genes.

In embodiments, the concept of highest multiple interdependence redundancy is used for reassignment of clusters, evaluation of fitness, mutation and candidate selection. It has proven to be a very powerful concept to base the various elements of the genetic algorithm on the concept of highest multiple interdependence redundancy.

According to a second aspect of the present invention there is provided a computer program product, when in use on a computer, to cause a system to perform method of the first aspect of the present invention.

According to a second aspect of the present invention there is provided a system for selecting a set of candidate genes from a pool of genes, the system comprising:
 a computing unit arranged to:
 receiving a set of gene data;
 cluster the set of gene data into a set of clusters with similar profiles by use of a clustering algorithm; and
 evolve the set of clusters by a genetic algorithm to select a set of candidate genes from the set of clusters.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

In the following embodiments are described in connection with gene expressions obtained from oligonucleotide microarray data. It is however within the ability of the skilled person to generalize the description to gene expressions obtained from any type of experiment. In example embodiments, the gene data may be obtained from microarray data in general, DNA-based array, differential DNA methylation arrays, chromatin immunoprecipitation on chip (ChIP) or methylation and gene number variations.

Figure 1:
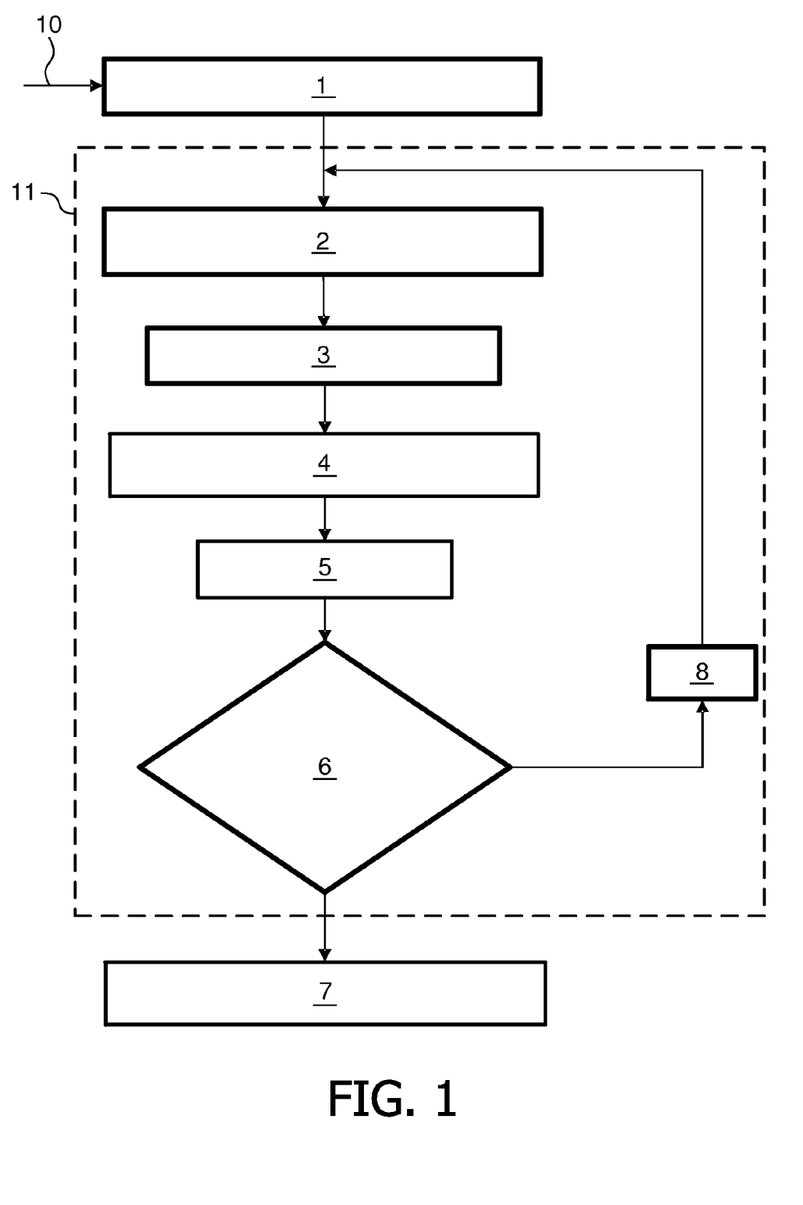
FIG. 1 illustrates an overall flow chart of the Evolutionary Clustering Algorithm (ECA)
Figure 2:
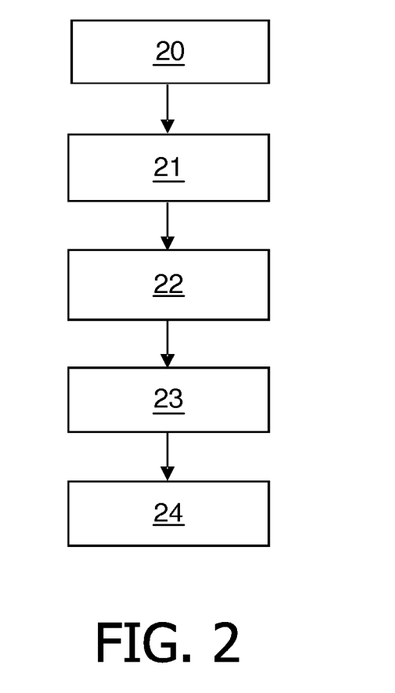
FIG. 2 schematically illustrated a flow chart of the mutation process.
Figure 3:
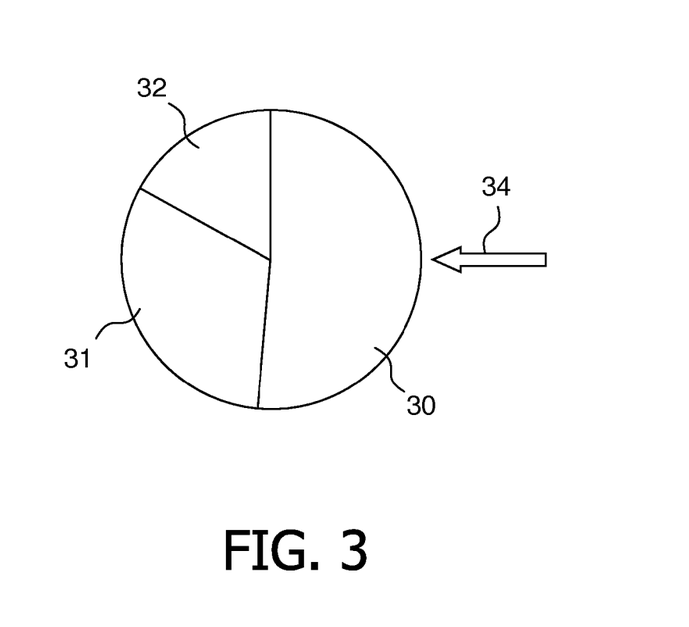
FIG. 3 schematically illustrates an embodiment of a roulette wheel used for selecting individuals for the next generation.

First the method is described at an overall level in connection with FIGS. 1 to 3 and secondly examples are provided where the method has been applied to gene data.

The gene expression values in a microarray are typically continuous which need to be discretized into proper intervals for computing an information measure. Usually the data contains noise from measurement errors or incorrect entry of the values. Noise can create a large number of intervals in the discretization result. Since more intervals lead to a greater loss in information, these problems need to be taken into account in the discretizing of the data.

In an embodiment Optimal Class Dependent Discretization (OCDD) algorithm is used to discretize the continuous data, as it gives a nearly global optimal solution. The OCDD algorithm is published by Wong et al., "A global optimal algorithm for class dependent discretization of continuous data, *Intelligent Data Analysis* 8(2), p 151-170, 2004. The OCDD takes into account the interdependence between the classes and the gene expression values and minimizes the information loss. Classes are defined as the categories to which each sample belongs. In this context, there are two classes—normal and diseased. To circumvent the problems while dealing with real data, smoothing of the data and a statistical test, for example the chi square test, is performed. Smoothing is done to remove noise before performing discretization and chi square test is done to reduce the number of intervals. The smoothing, chi square test and the parameter values used are essentially the same as described in the OCDD algorithm.

FIG. 1 illustrates an overall flow chart of an embodiment of the present invention. The general algorithm of embodiments of the present invention is referred to as an Evolutionary Clustering Algorithm (ECA). In the ECA, a set of gene data is received 10 for further processing.

As a pre-processing step, gene expression data which are similar for the disease class and the non-disease or normal class are removed in order to reduced the number of gene expressions.

Step 1: the First Generation is Obtained.

The first generation is obtained by arranging the set of gene expression data into a set of clusters with similar expression profiles by use of a clustering algorithm.

In an embodiment, the cluster algorithm employs an interdependence redundancy measure as distance measure. As an instance of a suitable cluster algorithm, the model Clustering by Mutual Information (CMI) as published by Au et al. "Attribute Clustering for Grouping, Selection and Classification of Gene Expression Data", *IEEE/ACM Transactions on Computational and Bioinformatics* 2(2): p 83-101, 2005 is used. Other algorithms, such as hierarchical, shrunken centroids etc. may also be used.

The genetic distance measure being employed is an information theoretic measure referred to as the interdependence redundancy measure. This measure takes into account interdependence between genes. Interdependence redundancy measure between two genes, x and y, having n attributes is given by:

$$IR(x:y) = \frac{M(x:y)}{E(x:y)}$$

where $$M(x:y) = \sum_{k=1}^{g} \sum_{l=1}^{h} P(v_k \wedge v_l) \log \frac{P(v_k \wedge v_l)}{P(v_k)P(v_l)},$$

$$E(x:y) = -\sum_{k=1}^{g} \sum_{l=1}^{h} P(v_k \wedge v_l) \log P(v_k \wedge v_l),$$

M(x: y) is the mutual information, E(x: y) is the joint entropy, g is the number of intervals of x, h is the number of intervals of y, $v_k$ is the $k^{th}$ interval of x, $v_l$ is the $l^{th}$ interval of y, $P(v_k \wedge v_l)$ is the probability of a genic value occurring in the interval $v_k$ and $v_l$ $P(v_k)$ is the probability of a value occurring within the interval $v_k$ and $P(v_l)$ is the probability of a value occurring within the interval $v_l$.

Although mutual information provides the knowledge about the mutual dependence of two genes, say x and y, its value increases with the number of possible gene expression values. Hence to find the correct distance measure between genes, mutual information is normalized by the entropy measure. This normalized information measure is called as the Interdependence Redundancy (IR(x:y)) measure. It is calculated as shown in the above equation. It reflects the degree of deviation from independence between two genes.

From the CMI a first set of clusters are obtained and these clusters are carried through to a genetic computation for selecting the candidate genes.

Before proceeding, two additional concepts are defined. First the so-called multiple interdependence redundancy (MIR) is defined. The MIR of a gene (x) is defined as the sum of its IR measure with all the other genes belonging to the same cluster:

$$MIR(x) = \sum_{(x,y \in C_k)} IR(x:y)$$

where y represents the genes in the same cluster as x.

Secondly, the mode (M) of a cluster is defined as the gene in the cluster having the highest MIR.

The set of clusters are inputted into a genetic algorithm 11 to find a set of candidate genes from the set of clusters.

In an embodiment, a set of individuals are created based on the clusters and it is the individuals that are inputted into the genetic algorithm. Each individual is represented as an array of numbers of which each index represents the corresponding gene from the gene expression data. The value at each index represents the cluster to which it belongs.

A set of unique genes is in the first generation chosen randomly and assigned as the mode for each cluster. The number of unique genes is set to be equal to the number of clusters. The remaining genes are then assigned to the clusters on the basis of their highest IR measures with the corresponding modes of the respective clusters. The other individuals in the population are created in similar fashion. The total number of genes in an individual is constant and has the same value as any other individual. A diverse set of individuals having different types of gene distributions in the clusters is thus generated. The population size is optimized to be 300 based on a study of the effects of population size.

Step 2: Fitness and Mode Calculation

In a second step 2, that is a first iteration or evolution, the fitness and the modes of the cluster are calculated for each individual. The individual with the highest fitness value is the fittest individual in the population. The fitness of an individual is the sum of the multiple interdependency measures of the total number of clusters. It is defined as:

$$F = \sum_{i=1}^{k} R_i$$

where F is the individual fitness, i denotes the cluster number and $R_i$ is the multiple interdependence redundancy measure of the mode of the cluster i.

Step 3: Cluster Assignment

The cluster assignment is based on use of a Cluster Assignment Operator. In the cluster assignment, the mode (M) of each cluster is identified. Other genes are assigned to respective clusters having higher IR with the cluster mode i.e. IR $(x:M_k)$, where $M_k$ is the mode of the $k^{th}$ cluster.

Step 4: Probabilistic Mutation Operator

The mutation rate is a user defined input. The best 5% of the population is retained to prevent loss of better fit individuals and increase the efficiency of the genetic algorithm. The remaining 95% of the individuals are stochastically selected for mutation. To select an individual for mutation, a random number is generated. An individual out of the total population is selected for mutation if the random number is less than the mutation rate. For the selected individual, in a cluster having at least five genes, a gene having the least MIR measure is chosen for donation to another cluster of the same individual. The relative distributions of the values of the IRs of the gene with the modes of the clusters is used to construct a roulette wheel. The cluster to which this gene is transferred is selected stochastically using the roulette wheel selection. The new modes of the clusters and the fitness of the individual are calculated. Once all the clusters have undergone the mutation, a mutated individual is created. Then the new population consists of the best 5% of the population, the mutated individuals and the unmutated individuals. The unmutated individuals are taken from the sorted population having lower fitness value in the population. This has been done to remove the bias due to selection of best 5% of the population, avoid premature convergence, bring diversity and allow the worse individuals to evolve. The probabilistic mutation rate is optimized to be 0.1 after analysing the effects of mutation rates (data not shown).

The mutation process is schematically illustrated in the flow chart of FIG. 2. The population is as a first step 20 set to be M large. The mutation rate is set 21 to be e.g. 0.1 and the individuals to be mutated is found as M'. In gene with the least MIR is found 22 in each cluster of a mutated individual. These genes are transferred 23 probabilistically to another cluster by use of the roulette wheel method. Finally, the new individuals 24 for the next generation are the unmutated individuals and the mutated individuals.

Step 5: Selection

Roulette wheel selection method is used for selecting all the individuals for the next generation. It is a popular selection method used in genetic algorithm. A roulette wheel is constructed from the relative fitness (ratio of individual fitness and total fitness) of each individual. It is represented in the form of a pie chart where the area occupied by each individual on the roulette wheel is proportional to its relative fitness. The sum of relative fitness (S) is calculated. A random number in the interval of 0 and S is generated. The population is traversed and then the corresponding relative fitness values are summed. When the sum is greater than the random number generated, the corresponding individual is selected. Since an individual with better fitness value will occupy a bigger area in the pie chart, the probability of selecting it will also be higher.

The selection process is schematically illustrated in the flow chart of FIG. 3 exemplified with three individuals. The fittest individual 30 is given the largest share in the roulette wheel and the weakest individual 32 is given the smallest share in the selection.

The remaining individuals 31 are shares being proportional to their relative fitness. A selection point is set 34 to find the individual for mutation.

6: Evaluate Fitness of Individuals

The variation of the mean fitness for ten consecutive generations is evaluated. If the variations of the mean fitness is less than 2%, the algorithm is terminated 7. If this is not the case a new generation is created 8. As an example, at the $n^{th}$ generation, the percentage difference between the mean fitness of the $(n-i)^{th}$ generation and the $(n-10)^{th}$ generation are calculated, where i varies from 0 to 9. If all these ten differences are less than 2%, the program execution is terminated, else it proceeds to the next generation.

7: Candidate Genes

The individual with the highest fitness is selected and the candidate genes are the genes of this individual.

EXAMPLES

Tests are performed on a 3.0 GHz dual core Intel xeon processor with 2 GB RAM. The whole work has been implemented in Java version 1.6.0. It has been divided into three segments—discretization, calculation of redundancy and ECA. Time taken for discretization for a set of 7129 genes and 30 samples is 0.6469 minutes, where the total number of interval produced is 55337. For the same dataset, the calculation of redundancy takes 1363.3997 minutes and one simulation of ECA takes 48.6153 minutes. The equilibrium generation ranges between 12 and 14. For the same set of data, one simulation of CMI takes 0.7068 minutes and takes 2 to 4 iterations for convergence and one simulation of k-means for 10000 iterations takes 70.56 minutes. For higher number of iterations, k-means showed recurrence of the solution more than once, which means the solution is likely to be a statistically optimal solution.

Synthetic Data:

To analyze the efficiency of the algorithm for clustering data, studies on two different synthetic data are performed initially. Each dataset contains 200 samples and 20 genes. The expression values vary from 0.0 to 1.0 such that the domain is divided into two intervals. The two intervals are [0.0, 0.5] and (0.5-1.0]. The first dataset comprises of two clusters and three classes as defined below. The range of values of genes $G_1$ and $G_2$ are used to define the values of other genes. $G_1$ defines the values of genes $G_3$ to $G_{11}$ such that $G_3$ to $G_6$ are in the same range as $G_1$ and $G_7$ to $G_{11}$ are in the opposite range. Similarly, $G_2$ defines the values of $G_{12}$ to $G_{20}$. The values of $G_{12}$ to $G_{15}$ are in the same range as of $G_2$ and that of $G_{16}$ to $G_{20}$ are in the opposite range. The samples for which $G_1$ and $G_2$ ranges from 0.0 to 0.5 are assigned class label 1. Class label 2 is assigned to the samples for which $G_1$ and $G_2$ ranges from 0.5 to 1.0 and the rest of the samples are assigned class label 3. The second dataset comprises of four clusters and five classes and the expression values vary from 0 to 10. The method adapted for generating the second dataset is similar to the method described for the first dataset. Equal width discretization is used to discretize the synthetic datasets. For both these datasets, it is seen that for all the simulations the ECA correctly identifies gene distribution in the clusters. But the CMI is able to group on an average 65% genes correctly (not shown).

Real Data:

The performance of ECA is evaluated on three gene expression data sets:

gastric cancer dataset, published by Tsutsumi, S. et al. (2002) Global gene expression analysis of gastric cancer by oligonucleotide microarrays. *Cancer Res* 1; 62(1): 233-40;

colon cancer dataset, publised by Alon, U., et al. (1999) Broad Patterns of Gene Expression Revealed by Clustering Analysis of Tumor and Normal Colon Tissues Probed by Oligonucleotide Arrays. *Proc. Nat'l Academy of Sciences of the United States of America.* 96(12): 6745-6750; and brain cancer [medulloblastoms metastasis] dataset, published by MacDonald, T. J., et al. (2001) Expression profiling of medulloblastoma: PDGFRA and the RAS/MAPK pathway as therapeutic targets for metastatic disease. Nat Genet. October; 29(2):143-52.

Descriptions of all the datasets are given in the Table 1.

TABLE 1

|  | gastric cancer | colon cancer | brain cancer |
| --- | --- | --- | --- |
| Number of genes | 7129 | 2000 | 2059 |
| Number of total samples | 30 | 62 | 23 |
| Number of diseased samples | 22 | 40 | 10 |
| Number of healthy samples | 8 | 22 | 13 |
| Number of clusters | 4 | 10 | 6 |
| Minimum gene expression value | 0.1 | 5.82 | 0.5 |
| Maximum gene expression value | 14,237.70 | 20,903.18 | 1,84,262.25 |

For each dataset, 50 simulations of CMI are performed. The number of clusters vary from 2-20 for each of these simulations. The cluster showing the highest individual fitness becomes the optimal cluster of the dataset for that simulation. The smallest value is chosen because the number of clusters should not be large as it would then scatter the data. The smallest value of the optimal cluster number among the 50 simulations is used as the optimal cluster number for the dataset. For all the algorithms the same cluster number is used for all the simulations.

ECA is compared with k-means and CMI. For the purpose of comparison, ten simulations for each of the algorithms are considered. For each simulation, a set of clusters is obtained. A subset of genes called as the candidate genes, is selected from each cluster for the classification studies. These candidate genes are composed of the top ranking genes. In the case of ECA and CMI, the top ranking genes are defined as the genes having the highest multiple redundancy measure in clusters. For k-means, they are the genes having the least Euclidian distance from the mean of the cluster. For classification accuracy calculation, leave-one-out cross validation (LOOCV) method is used. For LOOCV, one sample is selected as the test set and the remaining samples as the training set. The process is repeated through all the samples. Classification accuracy is calculated as the percentage of the test samples correctly predicted as either diseased or normal. A higher value of classification accuracy represents the better efficiency of the algorithm in selecting the significant genes that contain the most diagnostic information.

Example A

Studies on Gastric Cancer Dataset (GDS1210)

Average classification accuracy of top ranking genes is calculated for each of the algorithms. Table 2 shows one instance of gastric cancer dataset (other data not shown). The percentage difference of classification accuracy of ECA over CMI and k-means are computed. It represents the improvement of ECA over other algorithms.

TABLE 2

| | Top 2 genes per cluster | | |
| --- | --- | --- | --- |
| Simulations | ECA | CMI | K-means |
| 1 | 73.33 | 83.33 | 63.33 |
| 2 | 96.67 | 73.33 | 70.00 |
| 3 | 96.67 | 86.67 | 73.33 |
| 4 | 96.67 | 76.67 | 63.33 |
| 5 | 96.67 | 83.33 | 73.33 |
| 6 | 96.67 | 76.67 | 73.33 |
| 7 | 80.00 | 93.33 | 70.00 |
| 8 | 76.67 | 73.33 | 73.33 |
| 9 | 73.33 | 73.33 | 73.33 |
| 10 | 96.67 | 63.33 | 63.33 |
| Average | 88.34 | 78.33 | 69.66 |

Improvement of ECA over CMI and k-means with respect to top ranking genes for gastric cancer dataset is shown in Table 3. The studies show that ECA outperforms CMI and k-means.

TABLE 3

| | % improvement of ECA over | |
| --- | --- | --- |
| Top genes per cluster | CMI | k-means |
| 1 | 4.4 | 1.99 |
| 2 | 11.32 | 21.15 |
| 3 | 5.17 | 29.66 |
| 4 | 5.86 | 24.14 |
| 5 | 6.55 | 25.18 |

Corresponding to a different set of initial conditions for the gene distributions in the clusters, a number of simulations are considered. A comprehensive analysis of the algorithms on gastric cancer dataset shows that the number of simulations containing the top ranking genes that provide higher classification accuracy of test samples are more in the ECA than the CMI and the k-means. This proves that, in the ECA, there is a higher probability of finding the correct candidate genes than the others. Individual performance of classification accuracy for the ten simulations of the ECA, CMI and k-means are shown in Table 4. The table shows the number of simulations for different numbers of top ranking genes showing the corresponding classification accuracy.

TABLE 4

| Genes per cluster | % classification accuracy ||||||||
|---|---|---|---|---|---|---|---|---|
| | >60 & <=80 ||| >80 & <=95 ||| >95 & <100 |||
| | ECA | CMI | k-means | ECA | CMI | k-means | ECA | CMI | k-means |
| Top 1 | 5 | 7 | 3 | 3 | 3 | 7 | 2 | — | — |
| Top 2 | 4 | 6 | 10 | — | 4 | — | 6 | — | — |
| Top 3 | — | 2 | 10 | — | 1 | — | 10 | 7 | — |
| Top 4 | — | 2 | 7 | — | 1 | 3 | 10 | 7 | — |
| Top 5 | — | 2 | 10 | — | 2 | — | 10 | 6 | — |
| Top 6 | — | 2 | 10 | — | 1 | — | 10 | 7 | — |

Analysis of Classificatory Genes

Further, on studying the decision tree built by C4.5 on the genes subset, it is seen that the cases showing 96.67% classification accuracy use only one gene, either TGIF1 or in some cases D26129. A literature survey shows that TGIF1 plays an important role and its lower expression is correlated significantly with the metastasis of lymph node and may inhibit the invasion and metastatis of gastric cancer via the downregulation of MMP9 and VEGF proteins. D26129 is also an important gene associated with the progression of gastric cancer. A brief study on the ranking of the above two classificatory genes by CMI and k-means is done. Table 5 shows the comparative ranking of the genes in all the three algorithms. The two genes TGIF1 and D26129 are ranked very low by k-means and comparatively lower by CMI, too. In Table 5, the numbers below the name of each algorithm indicate the positions of the corresponding genes in the respective clusters (shown in square brackets) for three different simulations. All the 10 simulations of ECA has shown 96.67% classification accuracy with top 3 ranking genes. Since either gene TGIF1 or D26129 can only achieve 96.67% accuracy value, either of the genes must be ranked among the top 3 ranking genes. We can therefore conclude that the ECA is effective in picking out genes which contain significant diagnostic information for a particular disease.

TABLE 5

| D26129 Position of genes [Cluster No.] ||| TGIF1 Position of genes [Cluster No.] |||
|---|---|---|---|---|---|
| ECA | CMI | k-means | ECA | CMI | k-means |
| 1 [3] | 812 [1] | 412 [3] | 1 [3] | 3 [1] | 5854 [1] |
| 1 [3] | 706 [1] | 414 [3] | 2 [1] | 38 [3] | 5854 [4] |
| 2 [1] | 7 [3] | 412 [1] | 1 [1] | 25 [1] | 5854 [4] |

A comparative study of the three algorithms based on the common genes found across all the simulations above a threshold level of classification accuracy has been done. A set of top ranking genes i.e. top 1, 2 and 3, as shown in Table 6, is selected from each simulation. The genes recurring in all these simulations are called as the common genes.

TABLE 6

| genes per cluster | common genes ||| % classification accuracy |||
|---|---|---|---|---|---|---|
| | ECA | CMI | k-means | ECA | CMI | k-means |
| 1 | 1 | 2 | 2 | 76.67 | 76.67 | 73.33 |
| 2 | 4 | 5 | 3 | 80.00 | 73.33 | 76.67 |
| 3 | 6 | 8 | 4 | 96.67 | 96.67 | 76.67 |

A list of the top ranking common genes that is obtained using ECA for the top 6 ranking genes is given in Table 7(a). Table 7(b) contains the genes that are found to be significant in the classification process done by C4.5 decision tree i.e. those genes which are used as the nodes in constructing the decision tree.

TABLE 7(a)

| Genes | Functions |
|---|---|
| TGIF1 | Low expression is significant in metastasis; may inhibit invasion by down regulation of two other genes; has functions in transcription co-repressor activity and regulation of transcription |
| X90840 | mRNA for axonal transporter of synaptic vesicles |
| IGFBP4 | Role in cancer poorly defined; over expression leads to reduced growth in some cancers; seems to be highly expressed in a study on gastric cancer; locally available IGFs appear to stimulate mitogenesis; involved in DNA metabolism, cell proliferation, regulation of cell growth and signal transduction |
| HMHA1 | Histocompatibility minor (HA-1); expression found in many solid tumour cells; function involves intracellular signaling cascade also |
| CUL5 | Shows moderate expression in gastric cancer; has role in cell growth and proliferation also |
| QSCN6 (QSOX1) | Potentially involved in cell growth and highly induced in quiescent cells; thus inhibition of QSCN6 could play a role in cancer |
| COPS5 | Translation initiator factor activity involved in regulation of progression through cell cycle |
| UBE4A | Involved in ubiquitin dependent protein catabolic processes; get down regulated in diffuse type gastric cancer |
| LOC440345 | A hypothetical protein |
| CCL4 | Has roles in cell motility and signal transduction |
| ACAT1 | Acetyl Co-A c-acetyltransferase activity; involved in fatty acid metabolism |

TABLE 7(b)

| Genes | Functions |
|---|---|
| TGIF1 | Refer Table 8(a) |
| D26129 | Associated with progression of gastric cancer |

Comparison of Algorithms Based on Representative Genes

Figure 4:
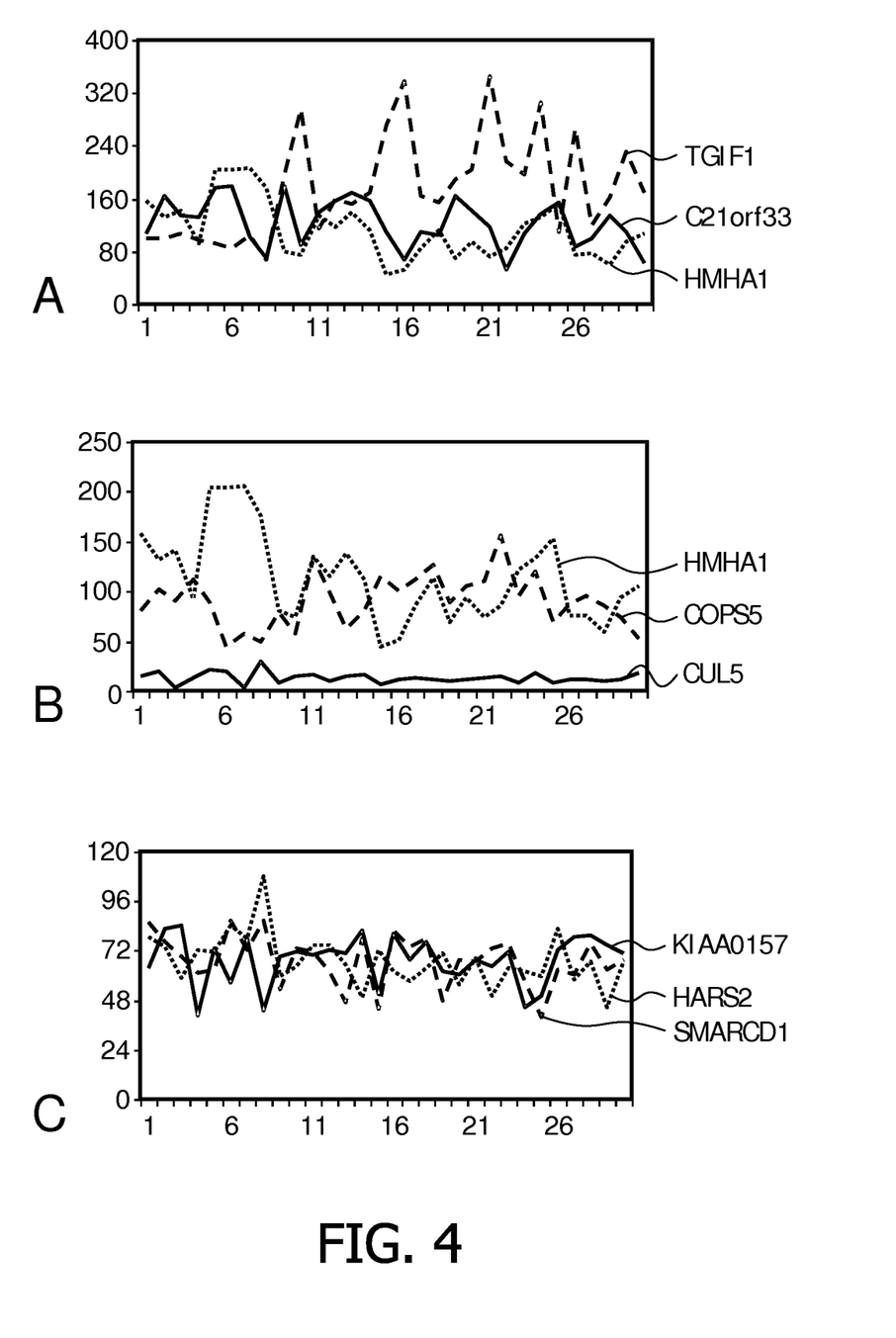
FIGS. 4A to 4C show gene expression values for a number of samples.

The collective trend of the expression levels of a group of co-expressed or co-regulated genes is described by the degree of coherence. Similarity among the genes takes into account only the genetic distances whereas the interdependence takes considers the genetic distance as well as the negative and positive correlations among the genes. For a pair of genes, the degree of coherence can be measured in the sense of similarity or positive/negative correlation. To study the coherence pattern, three representative genes are selected from the top five genes and their patterns are examined across different clusters for each algorithm. For ECA and CMI, the most significant genes in different clusters are selected based on the magnitude of their multiple interdependency measures. For k-means, those genes which show lesser distance from the mean of the clusters are chosen. The pattern of coherence of these genes for the algorithms—ECA, CMI and k-means are shown in FIG. 4A to 4C respectively for a single simulation chosen randomly. The Figure show gene expression values along the vertical axis for a number of samples plotted along the horizontal axis.

FIG. 4A presents the normal line graph of the expression pattern of 3 representative genes for cluster 1 of a single simulation for the ECA algorithm for gastric cancer dataset. FIG. 4B shows the normal line graph of the expression pattern of 3 representative genes for cluster 2 of a single simulation for the CMI algorithm for gastric cancer dataset. FIG. 4C gives the normal line graph of the expression pattern of 3 representative genes for cluster 3 of a single simulation for the k-means algorithm for gastric cancer dataset.

In ECA, the HMHA1 and TGIF1 genes are interdependent as they show negative correlation in their overall expression profile shape although they are not similar because of the large genetic distance between them. The HMHA1 and C21orf33 genes are similar in their expression profile and show negative correlations in some regions of the profile. The TGIF1 and C21orf33 genes show regions of positive and negative correlations across the expression profile shape. The CMI also shows the interdependence even though the genes are not similar due to large scaling factor as shown by the HMHA1 and CUL5 genes. The HMHA1 and COPS5 genes are similar and also show negatively and positively correlated regions across the profile. But the k-means algorithm shows coherence only in the similarity sense and does not take into account the scaling factors or interdependence for all the genes.

Thus, it can be concluded that while the Euclidean distance takes into consideration only similarity for clustering the genes, the interdependence redundancy measure can cluster the genes using both similarity and interdependence. It is seen that ECA is able to group the genes which show correlations in their overall expression profile shape as opposed to the small regions across the profile shape. Also, ECA takes into consideration larger scaling factors in comparison to CMI. From these results, it can be concluded that ECA is more coherent in clustering genes as compared to CMI. This shows that although ECA and CMI use the same distance measure, i.e., interdependence redundancy measure for clustering, ECA utilizes better the interdependence measure compared to CMI for clustering the genes.

Study of Gene Distribution in Clusters

The clusters formed by ECA consist of more or less the same number of genes (data not shown). Thus the genes in different clusters are more or less evenly distributed. The top ranking genes, thus selected, provide significant and insightful information. This is evident by a higher accuracy level in classifying the test samples when those top ranking genes are used. Thus the cluster configuration obtained by ECA are more reliable to select the top genes. But the k-means algorithm produces the most lopsided distribution (data not shown). The Gene distribution in the k-means algorithm is highly lopsided in most of the cases. Compared to the k-means algorithm, CMI shows better performance, i.e. even distribution pattern in many cases (data not shown). But it is poor in comparison to the ECA.

A randomly selected single simulation for each of the ECA, CMI and k-means algorithms shows the following trend of gene distributions in different clusters. As an example, the ECA has partitioned 7129 genes into four different clusters as 1911, 1786, 1628 and 1804 whereas the CMI has clustered the same number of genes into 2280, 2752, 1767 and 331 genes. An example of lopsided distribution in the k-means algorithm looks like: 458, 25, 6545 and 101 genes. The gene distribution also shows a better performance of ECA over CMI and k-means algorithms.

Example B

A Brief Study on Colon Cancer Dataset

For the purpose of comparison, the average classification accuracies of the test samples for all the ten simulations are calculated for each of the algorithms. The Table 8 shows one instance of the colon cancer dataset for the top 5 genes per cluster (other data not shown).

TABLE 8

| | TOP 5 genes per cluster | | |
|---|---|---|---|
| Simulation | ECA | CMI | k-means |
| 1 | 87.10 | 58.06 | 61.29 |
| 2 | 70.97 | 67.74 | 64.52 |
| 3 | 75.81 | 64.52 | 54.84 |
| 4 | 66.13 | 72.58 | 77.42 |
| 5 | 85.48 | 61.29 | 67.74 |
| 6 | 88.71 | 62.9 | 64.52 |
| 7 | 74.19 | 69.35 | 69.35 |
| 8 | 82.26 | 80.64 | 67.74 |
| 9 | 87.09 | 80.64 | 67.74 |
| 10 | 79.03 | 69.35 | 51.61 |
| Average | 79.68 | 68.71 | 64.68 |

To study the improvement of ECA over CMI and k-means algorithms in terms of classification accuracy, the percentage difference of the classification accuracy is computed. The improvement of ECA over CMI and k-means algorithms with respect to a few top ranking genes per cluster for the colon cancer dataset is shown in the Table 9. The comparative studies show that ECA outperforms CMI and k-means algorithms.

This colon cancer dataset has been extensively studied by Au et. al. (2005). Here our aim is limited to the analysis of the classification accuracy of the test samples as predicted by the top ranking genes. So we have purposefully omitted the analysis of the representative genes and the gene distribution in different clusters.

TABLE 9

| Top genes per cluster | % improvement of ECA over | |
|---|---|---|
| | CMI | k-means |
| 1 | 11.88 | 8.94 |
| 2 | 9.89 | 7.36 |
| 3 | 12.13 | 12.55 |
| 4 | 14.74 | 15.58 |
| 5 | 13.76 | 18.83 |

Example C

A Brief Study on Brain Cancer [Medulloblastoma Metastasis] Dataset (GDS232)

For each of the algorithms, the average classification accuracies for all the ten simulations are calculated. The Table 10 shows one instance of medulloblastoma metastasis dataset for the top one gene per cluster (other data not shown). In this case, too, we find a better performance of ECA over the other two algorithms in terms of the percentage difference in classification accuracy of the test samples. The studies show that the performance of ECA surpasses CMI and k-means algorithms.

TABLE 10

| | Top 1 gene per cluster | | |
|---|---|---|---|
| Simulations | ECA | CMI | k-means |
| 1 | 65.22 | 78.26 | 73.91 |
| 2 | 65.22 | 69.57 | 39.13 |
| 3 | 69.57 | 39.13 | 34.78 |
| 4 | 69.57 | 39.13 | 39.13 |
| 5 | 69.57 | 43.48 | 52.17 |
| 6 | 52.17 | 17.39 | 34.78 |
| 7 | 69.57 | 60.87 | 43.48 |
| 8 | 69.57 | 34.78 | 39.13 |
| 9 | 69.57 | 69.57 | 73.91 |
| 10 | 69.57 | 34.78 | 30.43 |
| Average | 66.96 | 48.7 | 46.09 |

The percentage improvement of ECA over CMI and k-means algorithms in terms of the classification accuracis predicted by the few top ranking genes per cluster for the gastric cancer dataset is shown in the Table 11.

TABLE 11

| | % improvement of ECA over | |
|---|---|---|
| Top genes per cluster | CMI | k-means |
| 1 | 27.28 | 31.17 |
| 2 | 34.78 | 15.53 |
| 3 | 23.57 | 13.38 |
| 4 | 5.15 | 0.00 |
| 5 | 14.69 | 5.59 |

A comprehensive analysis of the above three algorithms on brain cancer dataset shows that the number of simulations containing the top ranking genes that produce higher classification accuracy are more in ECA than in CMI or k-means algorithms. This proves that there is a higher probability of finding the correct candidate genes in ECA than those of CMI and k-means algorithms (data not shown). Here we have concentrated on proving only the superior performance of the present algorithm over CMI and k-means algorithms. It is seen that ECA, by and large, outperforms the other two algorithms in classification accuracy of the test samples by a small set of selected genes. For the gastric cancer, the colon cancer and the brain cancer datasets, the classification accuracies are calculated for the top ranking genes selected by ECA. Certain classification accuracies, when the top ranking genes alone are used, are higher than when the whole dataset is used for finding the classification accuracy. As an example, for the gastric cancer dataset, the classification accuracy is 93.33% when the whole dataset is taken into consideration. However, when any one of the significant classificatory genes (TGIF1/D26129) alone is used, the classification accuracy is 96.67%. This shows that ECA is able to select classificatory genes properly and effectively which can then be studied for their functional and diagnostic properties.

The present formalism of the ECA can be extended to the analysis of a three class microarray gene expression data. For example, a cancer microarray data can have samples of normal, mildly developed and fully diseased tissues. For this purpose, the discretization algorithm will be modified. This discretization process, especially smoothing of the data can be further improved to make the machine learning algorithm more effective. Other possible mutation operators can, in principle, be investigated to make the ECA more effective.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A computer-implemented method for selecting a set of candidate genes from a pool of genes, the method comprising:
receiving a set of gene data;
arranging the set of gene data into a set of clusters with similar profiles by use of a clustering algorithm, wherein the clustering algorithm employs an interdependence redundancy measure as distance measure; and
inputting the set of clusters into a genetic algorithm to select a set of candidate genes from the set of clusters, wherein in each evolution of the genetic algorithm, the genes are reassigned to clusters by first determining the gene of each cluster having the highest multiple interdependence redundancy and assigned other genes of the cluster in accordance with the genes having the highest interdependence redundancy.

2. The method according to claim 1, wherein the set of gene data comprises a subset relating to a disease condition and a non-disease condition, and wherein the set of gene data has been pre-processed to remove gene data which are similar in the disease condition subset and in the non-disease condition subset.

3. The method according to claim 1, wherein a set of individuals are inputted into the genetic algorithm, and wherein each individual comprises a set of individual genes, the set of individual genes being generated by assigning to the corresponding gene from the gene data to the indices and the value at each index to the cluster to which the gene is assigned.

4. The method according to claim 3, wherein fitness of an individual is determined based on the multiple interdependence redundancy of the clusters.

5. The method according to claim 4, wherein in individual for the next generation is selected based on a roulette wheel selection routine, where the roulette wheel is constructed from the relative fitness of each individual.

6. The method according to claim 5, wherein the set of candidate genes is selected as the individual with the highest fitness.

7. The method according to claim 6, wherein the genes of the individual is further ranked in accordance with the highest multiple interdependence redundancy.

8. The computer-implemented method according to claim 1, wherein the gene data is obtained from microarray data, DNA-based array, differential DNA methylation arrays, chromatin immunoprecipitation on chip (ChIP) or methylation and gene number variations.

9. The method according to claim 1, wherein the candidate genes are biomarkers for the disease of cancer, the biomarkers being selected from or any combination of the biomarkers: TGIF1, X90840, IGFBP4, CUL5, QSCN6 (QSOX1), COPS5, UBE4A, LOC440345, CCL4, ACAT1.

10. A computer program product, when in use on a computer, to cause a system to perform method of claim 1.

11. A system for selecting a set of candidate genes from a pool of genes, the system comprising:
a computing unit arranged to:
receive a set of gene data;
cluster the set of gene data into a set of clusters with similar profiles by use of a clustering algorithm; and
evolve the set of clusters by a genetic algorithm to select a set of candidate genes from the set of clusters.

12. The system of claim 11 wherein the clustering algorithm employs an interdependence redundancy measure as a distance measure, and wherein in each evolution of the genetic algorithm, the genes are reassigned to clusters by first determining the gene of each cluster having the highest multiple interdependence redundancy and assigned other genes of the cluster in accordance with the genes having the highest interdependence redundancy.

13. The system of claim 12. The method according to claim 1, wherein the set of gene data comprises a subset relating to a disease condition and a non-disease condition, and wherein the set of gene data has been pre-processed to remove gene data which are similar in the disease condition subset and in the non-disease condition subset.

14. The system of claim 12, wherein a set of individuals are inputted into the genetic algorithm, and wherein each individual comprises a set of individual genes, the set of individual genes being generated by assigning to the corresponding gene from the gene data to the indices and the value at each index to the cluster to which the gene is assigned.

15. The system of claim 14, wherein fitness of an individual is determined based on the multiple interdependence redundancy of the clusters.

16. The system of claim 15, wherein in individual for the next generation is selected based on a roulette wheel selection routine, where the roulette wheel is constructed from the relative fitness of each individual.

17. The system of claim 16, wherein the set of candidate genes is selected as the individual with the highest fitness.

18. The system of claim 17, wherein the genes of the individual is further ranked in accordance with the highest multiple interdependence redundancy.

19. The system of claim 12, wherein the gene data is obtained from microarray data, DNA-based array, differential DNA methylation arrays, chromatin immunoprecipitation on chip (ChIP) or methylation and gene number variations.

20. The system of claim 12, wherein the candidate genes are biomarkers for the disease of cancer, the biomarkers being selected from or any combination of the biomarkers: TGIF1, X90840, IGFBP4, CUL5, QSCN6(QSOX1), COPS5, UBE4A, LOC440345, CCL4, ACAT1.

* * * * *